United States Patent
Kiesl et al.

(10) Patent No.: US 6,977,499 B2
(45) Date of Patent: Dec. 20, 2005

(54) FORMATION-BASED INTERPRETATION OF NMR DATA FOR CARBONATE RESERVOIRS

(75) Inventors: Christian Kiesl, Hannover (DE); Thomas Kruspe, Wienhausen (DE); Holger F. Thern, Hannover (DE); Iris Surholt, Hannover (DE)

(73) Assignee: Baker Hughes Incorporated, Houston, TX (US)

(*) Notice: Subject to any disclaimer, the term of this patent is extended or adjusted under 35 U.S.C. 154(b) by 2 days.

(21) Appl. No.: 10/442,585

(22) Filed: May 21, 2003

(65) Prior Publication Data

US 2003/0231017 A1 Dec. 18, 2003

Related U.S. Application Data

(63) Continuation-in-part of application No. 09/928,768, filed on Aug. 13, 2001, now Pat. No. 6,727,696, which is a continuation-in-part of application No. 09/839,423, filed on Apr. 20, 2001, now Pat. No. 6,446,736, which is a continuation of application No. 09/247,340, filed on Feb. 9, 1999, now Pat. No. 6,247,542.

(51) Int. Cl.[7] ............................................... G01V 3/00
(52) U.S. Cl. ..................................................... 324/303
(58) Field of Search ........................................ 324/303

(56) References Cited

U.S. PATENT DOCUMENTS

| | | | | |
|---|---|---|---|---|
| 3,258,681 A | * | 6/1966 | Brown et al. | 324/303 |
| 3,439,260 A | * | 4/1969 | Bene | 324/303 |
| 3,528,000 A | * | 9/1970 | Schwede | 324/303 |
| 5,306,640 A | * | 4/1994 | Vinegar et al. | 436/29 |
| 5,680,043 A | | 10/1997 | Hurlimann et al. | 324/303 |
| 5,831,433 A | * | 11/1998 | Sezginer et al. | 324/303 |
| 6,040,696 A | * | 3/2000 | Ramakrishnan et al. | 324/303 |
| 6,069,477 A | | 5/2000 | Chen et al. | 324/303 |
| 6,088,656 A | * | 7/2000 | Ramakrishnan et al. | 702/13 |
| 6,111,408 A | * | 8/2000 | Blades et al. | 324/303 |
| 6,111,409 A | * | 8/2000 | Edwards et al. | 324/303 |
| 6,229,308 B1 | * | 5/2001 | Freedman | 324/303 |
| 6,232,778 B1 | * | 5/2001 | Speier et al. | 324/303 |
| 6,331,775 B1 | | 12/2001 | Thern et al. | 324/303 |
| 6,346,813 B1 | * | 2/2002 | Kleinberg | 324/303 |
| 6,369,567 B1 | * | 4/2002 | Song et al. | 324/303 |
| 6,559,639 B2 | | 5/2003 | Minh et al. | 324/303 |
| 6,570,382 B1 | * | 5/2003 | Hurlimann et al. | 324/303 |
| 6,571,619 B2 | * | 6/2003 | Herron et al. | 73/152.14 |
| 6,577,125 B2 | * | 6/2003 | Prammer et al. | 324/303 |
| 2002/0153888 A1 | | 10/2002 | Kruspe et al. | 324/303 |
| 2003/0231017 A1 | | 12/2003 | Kiesl et al. | 324/303 |

OTHER PUBLICATIONS

Flavio et al., "Quantitative Characterization of Carbonate Pore Systems by Digutal Image Analysis", AAPG Bulletin, V. 82 No. 10 Oct. 1998, P1815–1836.*
http://www.pe.utexas.edu/Dept/Academic/Courses/F2001/PGE368/PDFs/Petrophysical_Approach.pdf; "ThePetrophysical Approach", P1–24.*
http://www.scaweb.org/assets/pdf/scal–2000_carbonates.pdf," Carbonate Rocks"; P 1–10.*
J.O. Parra et al., "NMR Acoustic Signatures in Vuggy carbonate Aquifiers", 42nd Annual SPWLA Meeting, Jun. 2001, P1–12.*

(Continued)

Primary Examiner—Diego Gutierrez
Assistant Examiner—Dixomara Vargas
(74) Attorney, Agent, or Firm—Madan, Mossman & Sriram, P.C.

(57) ABSTRACT

An apparatus and method for determining a parameter of interest of a formation composed of carbonate rock. A nuclear magnetic resonance (NMR) sensor assembly produces a pulsed RF field designed for obtaining measurements indicative of the parameter of interest of the formation. A downhole processor processes the measurements for obtaining BVI and BVM using a cutoff time based on classification of the carbonate. Further processing is done to estimate the permeability of the carbonate.

31 Claims, 13 Drawing Sheets

OTHER PUBLICATIONS http://www.oilfield.slb.com/media/resources/ mewr/wer18/chapter2.pdf, "Carbonates the inside story", P1–17.* http://faculty.uaeu.ac.ae/~sadooni/reservoir/lecture1.htm, Quick introduction to "Carbonate Reservoirs", P1–16.*

Leslie A. Melim et al.; *The Importance of Pore Type on Permeability of Neogene Carbonates, Great Bahama Bank,* SEPM (Society for Sedimentary Geology), ISBN 1–56576–007–8, pp. 217–238.

http://www.pcai.com/web/ai info/expert systems.html; PCAI—Expert Systems; pp. 1–21.

http://www-ra.informatik.uni-tuebingen.de/SNSS/announce.html; What is SNNS? pp. 1–2.

T.S. Ramakrishnan et al.; *A Model–Based Interpretation Methodology for Evaluating Carbonate Reservoirs,* SPE 71704, 2001 SPE Annual Technical Conference and Exhibition held in New Orleans, Louisiana, Sep. 30–Oct. 3, 2001, pp 1–15, 13 Figs.

Mahmood Akbar et al.; *A Snapshot of Carbonate Reservoir Evaluation,* Oilfield Review, Winter 2000/2001, pp. 20–41.

Oxford University Press; xreter—Dunham classification, p. 1.

Bureau of Economic Geology, *Carbonate Classification by Interparticle Pore Space,* The University of Texas at Austin, Reservoir Characterization Research Laboratory, Rock Fabric Studies, pp. 1–2.

Carbonates: Classification; *The 'How–To' of Classification,* pp. 1–2.

Ben Lowden; *Some simple methods for refining permeability estimates from NMR logs and generating capillary pressure curves,* http://www.lps.org.uk/dialogweb/archive/permeability_estimates_lowden/lowden.html, pp. 1–7.

Frederick Hayes–Roth; *The Knowledge–Based Expert System: A Turtorial ,* vol. 17, No. 9, (ISSN 0018–9162) Sep. 1984, pp. 11–28, 3 Tables.

* cited by examiner

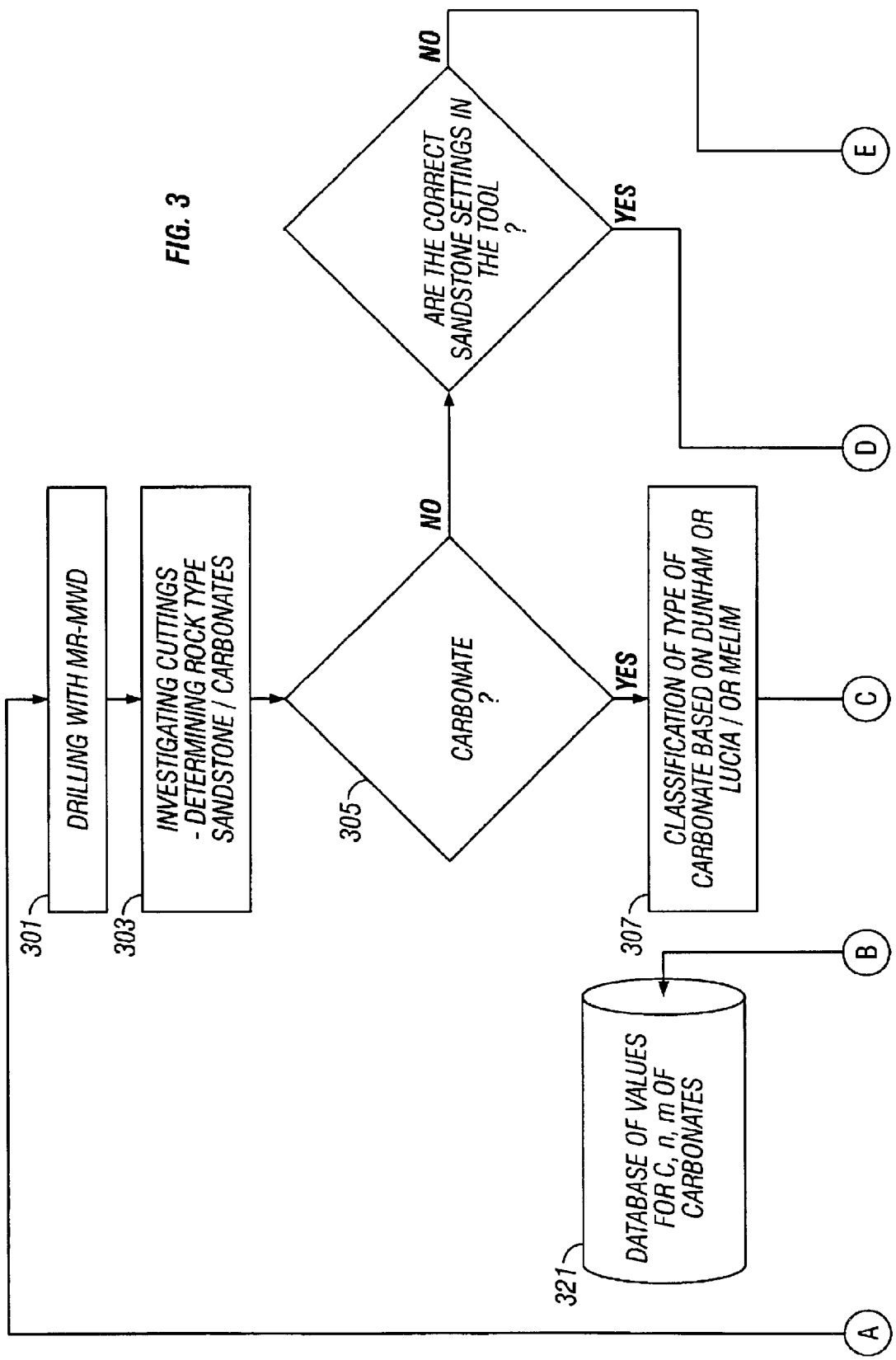

FORMATION-BASED INTERPRETATION OF NMR DATA FOR CARBONATE RESERVOIRS

CROSS REFERENCES TO RELATED APPLICATIONS

This application is a Continuation-in-part of U.S. patent application Ser. No. 09/928,768 filed on Aug. 13, 2001 now U.S. Pat. No. 6,727,696, which is a Continuation in part of U.S. patent application Ser. No. 09/839,423 filed on Apr. 20, 2001, now U.S. Pat. No. 6,446,736, which is a continuation of U.S. patent application Ser. No. 09/247,340 filed on Feb. 9, 1999, now U.S. Pat. No. 6,247,542.

BACKGROUND OF THE INVENTION

1. Field of the Invention

This invention is related to methods for acquiring and processing nuclear magnetic resonance (NMR) measurements for determination of longitudinal and transverse relaxation times $T_1$ and $T_2$ and related petrophysical properties. Specifically, the invention deals with use of an expert system downhole for acquiring and evaluating NMR measurements contemporaneous with the drilling of wells in a formation including a carbonate rock, and with use of a downlink communication from the surface for modifying the parameters of the downhole acquisition and processing system.

2. Description of the Related Art

Nuclear magnetic resonance is used in the oil industry, as well as other industries, including and particularly in certain oil well logging tools. NMR instruments may be used for determining, among other things, the fractional volume of pore space and the fractional volume of mobile fluid filling the pore space of earth formations. Methods of using NMR measurements for determining the fractional volume of pore space and the fractional volume of mobile fluids are described, for example, in "Spin Echo Magnetic Resonance Logging: Porosity and Free Fluid Index Determination," M. N. Miller et al., Society of Petroleum Engineers paper no. 20561, Richardson, Tex., 1990. Further description is provided in U.S. Pat. No. 5,585,720, of Carl M. Edwards, issued Dec. 17, 1996 and having the same assignee as the present application, entitled "Signal Processing Method For Multi-exponentially Decaying Signals And Applications To Nuclear Magnetic Resonance Well Logging Tools." The disclosure of that patent is incorporated herein by reference.

Deriving accurate transverse relaxation time $T_2$ relaxation spectra from nuclear magnetic resonance (NMR) data from logging subterranean formations, or from cores obtained from such formations, is critical to determining total and effective porosities, irreducible water saturations, and permeabilities of the formations. U.S. Pat. No. 6,069,477 to Chen et al. discusses the constituents of a fluid saturated rock and various porosities of interest. The total porosity as measured by a density logging tool is the difference between the total volume and the solid portion. The total porosity includes clay-bound water, capillary bound water, movable water and hydrocarbons. The effective porosity, a quantity of interest to production engineers, is the sum of the last three components and does not include the clay bound water. Accurate spectra are also essential to estimate $T_2$ cutoff values and to obtain coefficients for the film model or Spectral Bulk Volume Irreducible (SBVI) model. Effective porosities are typically summations of partial porosities; however, distortion of partial porosity distributions has been commonly observed for a variety of reasons. These reasons include poor signal-to-noise ratio (SNR), and poor resolution in the time domain of the NMR data.

The most common NMR log acquisition and core measurement method employs $T_2$ measurements using CPMG (Carr, Purcell, Meiboom and Gill) sequence, as taught by Meiboom and Gill in "Modified Spin-Echo Method for Measuring Nuclear Relaxation Time," Rev. Sci. Instrum. 1958, 29, pp. 688–691. In this method, the echo data in any given echo train are collected at a fixed time interval, the interecho time (TE). Usually, a few hundred to a few thousand echoes are acquired to sample relaxation decay. However, for determination of CBW, echo sequences of as few as ten echoes have been used.

There are numerous examples of wireline NMR logging tools used for obtaining information about earth formations and fluids after a wellbore has been drilled. The logging tools are lowered into the borehole and NMR signals are obtained using different configurations of magnets, transmitter coils and receiver coils. Rig time is expensive, so that the general objective in wireline logging is to obtain interpretable data within as short a time as possible. Depending upon the reservoir, different radio frequency (RF) pulsing schemes for generating RF fields in the formation have been used. The most commonly used pulsing schemes are the CPMG sequence and variations thereof. The parameters that may be varied include the wait time, the number of pulses within a CPMG sequence, and the time interval between the pulses. Long wait times are needed for proper evaluation of the long relaxation times of gas reservoirs while short wait times and/or short pulse spacings are used for evaluating clay bound water (CBW). For example, U.S. Pat. No. 6,331,775, issued to Thern et al, having the same assignee as the present application and the contents of which are fully incorporated herein by reference, discusses the use of a dual wait time acquisition for determination of gas saturation in a formation. U.S. Pat. No. 5,023,551 to Kleinberg et al discusses the use of CPMG sequences in well logging. U.S. Pat. No. 6,069,477 to Chen et al, the contents of which are fully incorporated herein by reference, teaches the use of pulse sequences with different pulse spacings to determine CBW. Phase alternated pairs (PAPs) of sequences are commonly acquired to reduce the effects of ringing.

The commonly used seven conductor wireline is not a serious limitation to two-way communication from the surface to the logging tool. This makes it possible to process data uphole with little or no downhole processing and to send instructions downhole to the logging tool to modify the acquisition schemes based on the surface processing.

In contrast, measurements made with a drilling assembly in the wellbore have several problems. First of all, there is little a priori information available about the actual subsurface formations except that inferred from surface seismic data. As would be known to those versed in the art, the resolution of such seismic data is of the order of several meters to tens of meters. This makes it difficult, if not impossible, to base an acquisition scheme on the basis of expected properties of formations.

Secondly, when the drilling assembly is in a borehole, data communication capability is in most cases severely limited. Telemetry is accomplished either by sending acoustic pulses through the mud or through the drillstring. The data rate with mud pulsing is limited to a few bits per second and communication through the drillstring becomes a serious problem when the drillbit is being operated due to the vibration and noise produced. This makes it impossible to evaluate acquired data at the surface and to modify the acquisition scheme based on this evaluation.

A third problem arises from the nature of NMR data itself. The sensitive volume of commonly used logging tools is no more than a few millimeters in thickness. The RF frequency is tuned to operate at the Larmor frequency corresponding to the static magnetic field in the sensitive volume. Any motion of the tool during drilling can mean that a RF-pulse reaches an area that has not been reached by an earlier excitation or refocusing pulse. This results in a severe degradation of the data. U.S. Pat. No. 5,705,927 issued to Kleinberg discloses making the length of each CPMG sequence small, e.g. 10 ms, so that the drill collar cannot be displaced by a significant fraction of the vertical or radial extent of the sensitive region during a CPMG pulse sequence. However using such short sequences and short wait times only gives an indication of the bound fluid volume and gives no indication of the total fluid volume.

The economic value of an oil and gas bearing formation depends on the amount of producible hydrocarbons contained in the subsurface reservoir. This amount of producible hydrocarbons is a function of the formation porosity and permeability.

NMR measurements for formation evaluation yield signals originating from the precessing protons of the fluids in the pore space of the rock. Due to interactions of the fluid molecules with each other or the pore walls, the signal of each proton decays exponentially with a characteristic time $T_2$ (longitudinal relaxation time).

Permeability is a function of, among other things, the $T_2$ distribution and the pore size distribution. In sandstones, where porosity and permeability is regular, this relationship is fairly consistent and NMR is a reliable method of characterizing reservoirs. Carbonate reservoir porosity and permeability are not so well defined as sandstone and the relationship varies with different lithofacies.

Siliciclastic sediments, such as sandstones and shale, develop through the attrition of other rocks. Their grains are sorted prior to deposition. Sandstones and shale are formed of sedimentary particles derived from sources outside the depositional basin. Siliciclastic sediments are relatively stable after deposition. As a result, the pore space in sandstones is mainly intergranular and its complexity depends on the degree of sorting.

Carbonates form in special environments and, in contrast to sandstones, are biochemical in nature. They are essentially autochthonous, as they form very close to the final depositional sites. They are not transported and sorted in the same way as sandstones. Carbonates are usually deposited very close to their source and develop as a result of various processes. Their texture is more dependent on the nature of the skeletal grains than on external influences. Intrabasinal factors control facies development. Reefs, bioherms, and biostroms are example of in-place local deposition where organisms have built wave-resistant structures above the level of adjacent time-equivalent sediments.

Carbonates are characterized by different types of porosity and have unimodal, bimodal, and other complex pore structure distributions. This distribution results in wide permeability variations for the same total porosity, making it difficult to predict their producibility. In this case, long echo trains with a large number of echoes and a long-prepolarization time may be applicable. Carbonate rock texture produces spatial variations in permeability and capillary bound water volumes.

Carbonates are particularly sensitive to post-depositional diagenesis, including dissolution, cementation, recrystallization, dolomitization, and replacement by other minerals. Calcite can be readily dolomitized, sometimes increasing porosity. Complete leaching of grains by meteoric pore fluids can lead to textural inversion which may enhance reservoir quality through dissolution or occlude reservoir quality through cementation. Burial compaction fracturing and stylolithification are common diagenitic effects in carbonates, creating high-permeability zones and permeability barriers or baffles, respectively. Diagenesis can cause dramatic changes in carbonate pore size and shape. On a large scale, porosity due to fracturing or dissolution of carbonate rocks can produce "pores" up to the size of caverns.

Given the wide range of origins for carbonate rocks, and the variety of secondary processes which may affect them, it is not surprising that the convoluted pore space of a carbonate may be quite different from that found in siliciclastic sediments. All carbonate sediments are composed of three textural elements: grains, matrix, and cement.

In general, geologists have attempted to classify sedimentary rocks on a natural basis, but some schemes have genetic implications (i.e., knowledge or origin of a particular rock type is assumed).

The relative proportions of the components, among others, can be used to classify carbonate sediments. A widely used classification scheme is proposed by Dunham (see Dunham, "Classification of carbonate rocks according to depositional texture", in *Classification of carbonate rocks—A Symposium*, Ham, ed., volume 1, pages 108–121. AAPG Mem., 1962.) In Dunham, carbonates are classified based on the presence or absence of lime mud and grain support. Textures range from grainstone, rudstone, and packstone (grain-supported) to wackestone and mudstone (mud-supported). Where depositional texture is not recognizable, carbonates are classified as boundstone or crystalline. Within these carbonates, the porosity takes many forms, depending on the inherent fabric of the rock, and on the types of processes that can occur during and after deposition.

In many carbonates, it is not possible to map the rock texture using conventional logs. Rock texture exerts a strong influence on permeability variations and bound water distributions—important factors in reservoir simulations. For example, while porosity logs may show little change between grainstones, wackestones and mudstones, the capillary-bound water volumes and permeabilities for these rocks may be very different.

Another classification system, by Lucia (see Lucia, Petrophysical parameters estimated from visual description of carbonate rocks: a field classification of pore space. Journal of Petroleum Technology, 35:626–637, March 1983) is based on petrographical attributes and porosity. Dolomites are included in this classification scheme.

Pore type characterization is used in a classification scheme of Choquette & Pray (see P. W. Choquette and L. C. Pray. Geologic nomenclature and classification of porosity in sedimentary carbonates. AAPG Bull., 54:207–250, 1970). Choquette & Pray, in contrast to Dunham, classify carbonates according to fabric and nonfabric pore types. Examples of the former are inter-and intraparticle porosity, while those of the latter are fractures and vugs. Another classification scheme, by Melim et al., differentiates between primary and secondary pore spaces using the description based on classification of Choquette & Pray. Some of the petrographical information obtained using these classifications are used to improve the petrophysical evaluation of the geological formations.

NMR logging tools use large magnets to strongly polarize hydrogen nuclei in water and hydrocarbons as they diffuse about and are contained in the pore space in rocks. When the magnet is removed, the hydrogen nuclei relax. The relaxation time, $T_2$, depends on the pore-size distribution; larger pores typically have longer relaxation times. Tar and viscous oils relax more quickly than light oil and water. The variations in relaxation time produce a $T_2$ distribution from which fluid components and pore sizes are interpreted. As is well known to those versed in the art, $T_1$ and $T_2$ distributions correlate very well if the diffusion is negligible. In this case, we assume that the cutoff values are equal. The method described herein is applicable for both $T_1$ and $T_2$ distributions.

Two standard permeability equations have been established for applications in the oil industry. The Schlumberger-Doll Research (SDR) equation uses simply the geometric mean of the measure $T_2$ distribution to derive permeability. The Timur-Coates equation uses a $T_2$ cutoff value that divides the $T_2$ distribution into a movable and an irreducible fluid saturation and relates these values to permeability. To improve the permeability prediction, the results of the classification and the data interpretation are used for a variation of the parameters of both equations. U.S. Pat. No. 6,559,639 to Minh et al. describes a method for determination of permeability using the sum of echoes. Other permeability models such as the Kozeny-Carman method may also be used for permeability determination.

Various methods have been proposed to determine formation properties of carbonates using Nuclear Magnetic Resonance. Hidajat et al. (see Hidajat et al., "Study of Vuggy Carbonates using X-Ray CT Scanner and NMR", SPE 77396, 2002) works to improve correlation between NMR $T_2$ response in carbonate systems, including the contributions of vugs to carbonate permeability. Ramakrishnan et al. (see Ramakrishnan et al., "A Model-based Interpretation Methodology for Evaluating Carbonate Reservoirs", SPE 71704, 2002) develops an integrated methodology for carbonate interpretation. The methodology of Ramakrishnan parametrizes the pore structure in terms of a multiporosity system of fractures, vugs, inter- and intragranular porosities. NMR data is useful in separating the inter- and intragranular components. The method of Ramakrishnan requires the use of more services than are normally run to provide data.

There is a need for an apparatus and method of obtaining NMR measurements while a wellbore is being drilled through a carbonate formation that is able to modify the acquisition and processing parameters with a minimum of communication with the surface. Such an invention should preferably be able to adjust the acquisition depending upon actual downhole conditions. The method should preferably be robust in the presence of vibration of the logging tool. There is also a need for evaluating carbonates using a method restricted to NMR and carbonate classification only. The present method satisfies this need.

SUMMARY OF THE INVENTION

The present invention is a method and system for determining a parameter of interest of an earth formation including a carbonate. A nuclear magnetic resonance (NMR) sensor assembly conveyed in a borehole in the earth formation is used for obtaining nuclear magnetic resonance (NMR) spin-echo signals indicative of the parameter of interest. A classification scheme is used for obtaining a class of the carbonate. A downhole processor is used for processing the spin-echo signals using the obtained class for obtaining the parameter of interest. carbonate. A downhole processor is used for processing the spin-echo signals using the obtained class for obtaining the parameter of interest.

One or more of several classification schemes including the Dunham, Lucia or Melim classification schemes may be used. The classifications may be based on examination of cuttings brought to a surface location by a drilling mud conveyed in said borehole. The processor uses processing parameters sent by telemetry to the downhole processor, or parameters retrieved from a downhole storage device based at least in part on using class information sent from a surface location by telemetry. One of the important processing parameter includes a cutoff time $T_{2\ cutoff}$ of a transverse relaxation time or $T_{1\ cutoff}$ of said spin echo signals, the cutoff time differentiating between a bound volume irreducible (BVI) and a bound water moveable (BVM).

The cutoff time is based on a database obtained from a large number of sample measurements. An equation relating the permeability of the carbonate to the previously determined parameters is used for obtaining an estimate of the carbonate permeability. The equation may be defined by one of (i) the Coates equation, (ii) the SDR equation, (iii) Kozeny-Carman method, and, (iv) the sum of echoes.

BRIEF DESCRIPTION OF THE DRAWINGS

The present invention is best understood with reference to the following figures in which like numbers refer to like elements.

DESCRIPTION OF PREFERRED EMBODIMENT

Figure 1:
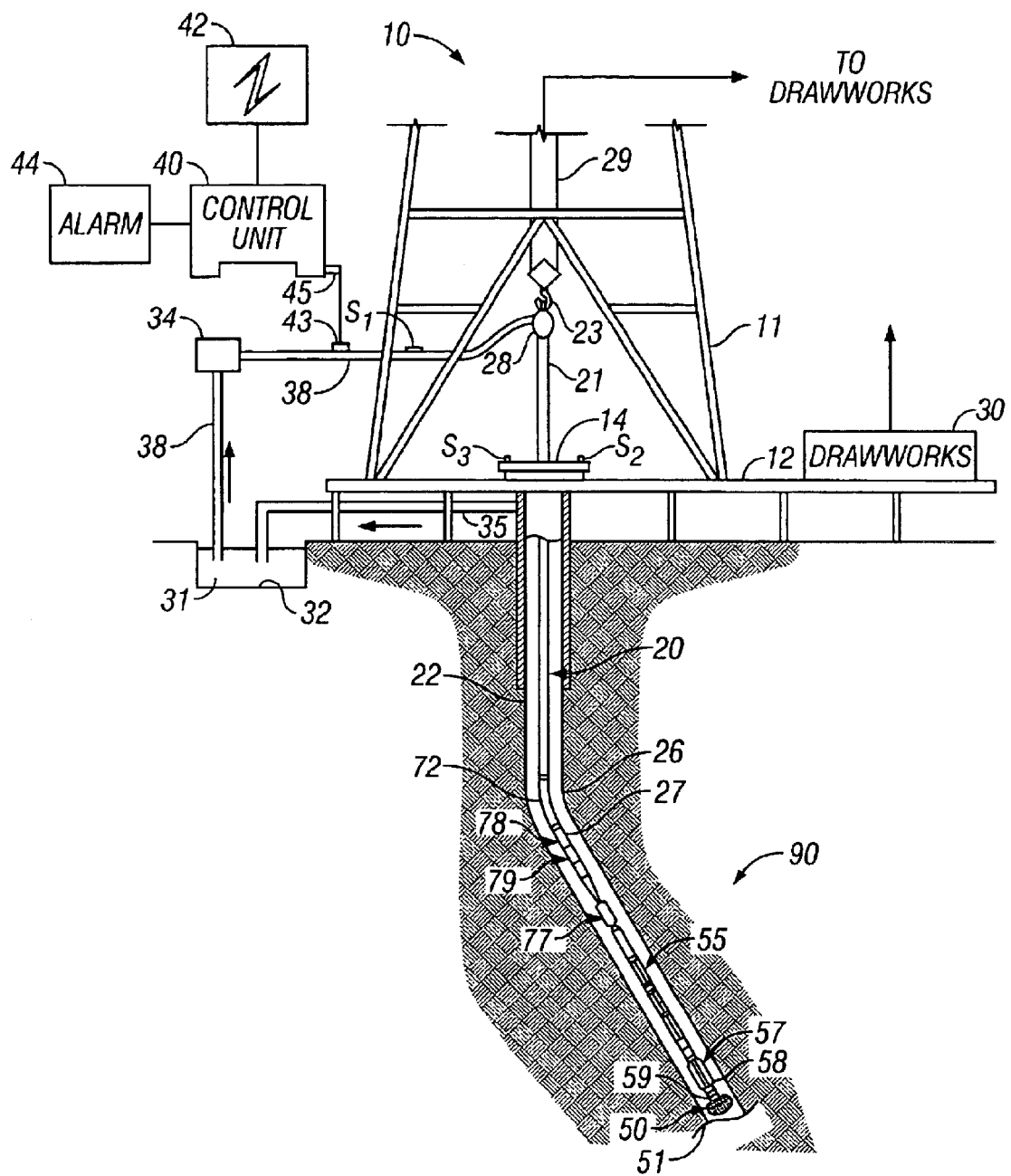
FIG. 1 (Prior Art) shows a drilling apparatus suitable for use with the present invention.

FIG. 1 shows a schematic diagram of a drilling system 10 with a drillstring 20 carrying a drilling assembly 90 (also referred to as the bottom hole assembly, or "BHA") conveyed in a "wellbore" or "borehole" 26 for drilling the wellbore. The drilling system 10 includes a conventional derrick 11 erected on a floor 12 which supports a rotary table 14 that is rotated by a prime mover such as an electric motor (not shown) at a desired rotational speed. The drillstring 20 includes a tubing such as a drill pipe 22 or a coiled-tubing extending downward from the surface into the borehole 26. The drillstring 20 is pushed into the wellbore 26 when a drill pipe 22 is used as the tubing. For coiled-tubing applications, a tubing injector, such as an injector (not shown), however, is used to move the tubing from a source thereof, such as a reel (not shown), to the wellbore 26. The drill bit 50 attached to the end of the drillstring breaks up the geological formations when it is rotated to drill the borehole 26. If a drill pipe 22 is used, the drillstring 20 is coupled to a drawworks 30 via a Kelly joint 21, swivel 28, and line 29 through a pulley 23. During drilling operations, the drawworks 30 is operated to control the weight on bit, which is an important parameter that affects the rate of penetration. The operation of the drawworks is well known in the art and is thus not described in detail herein.

During drilling operations, a suitable drilling fluid 31 from a mud pit (source) 32 is circulated under pressure through a channel in the drillstring 20 by a mud pump 34. The drilling fluid passes from the mud pump 34 into the drillstring 20 via a desurger (not shown), fluid line 28 and Kelly joint 21. The drilling fluid 31 is discharged at the borehole bottom 51 through an opening in the drill bit 50. The drilling fluid 31 circulates uphole through the annular space 27 between the drillstring 20 and the borehole 26 and returns to the mud pit 32 via a return line 35. The drilling fluid acts to lubricate the drill bit 50 and to carry borehole cutting or chips away from the drill bit 50. A sensor $S_1$ preferably placed in the line 38 provides information about the fluid flow rate. A surface torque sensor $S_2$ and a sensor $S_3$ associated with the drillstring 20 respectively provide information about the torque and rotational speed of the drilistring. Additionally, a sensor (not shown) associated with line 29 is used to provide the hook load of the drillstring 20.

In one embodiment of the invention, the drill bit 50 is rotated by only rotating the drill pipe 22. In another embodiment of the invention, a downhole motor 55 (mud motor) is disposed in the drilling assembly 90 to rotate the drill bit 50 and the drill pipe 22 is rotated usually to supplement the rotational power, if required, and to effect changes in the drilling direction.

In the preferred embodiment of FIG. 1, the mud motor 55 is coupled to the drill bit 50 via a drive shaft (not shown) disposed in a bearing assembly 57. The mud motor rotates the drill bit 50 when the drilling fluid 31 passes through the mud motor 55 under pressure. The bearing assembly 57 supports the radial and axial forces of the drill bit. A stabilizer 58 coupled to the bearing assembly 57 acts as a centralizer for the lowermost portion of the mud motor assembly.

In one embodiment of the invention, a drilling sensor module 59 is placed near the drill bit 50. The drilling sensor module contains sensors, circuitry and processing software and algorithms relating to the dynamic drilling parameters. Such parameters preferably include bit bounce, stick-slip of the drilling assembly, backward rotation, torque, shocks, borehole and annulus pressure, acceleration measurements and other measurements of the drill bit condition. A suitable telemetry or communication sub 72 using, for example, two-way telemetry, is also provided as illustrated in the drilling assembly 90. The drilling sensor module processes the sensor information and transmits it to the surface control unit 40 via the telemetry system 72.

The communication sub 72, a power unit 78 and an MWD tool 79 are all connected in tandem with the drillstring 20. Flex subs, for example, are used in connecting the MWD tool 79 in the drilling assembly 90. Such subs and tools form the bottom hole drilling assembly 90 between the drillstring 20 and the drill bit 50. The drilling assembly 90 makes various measurements including the pulsed nuclear magnetic resonance measurements while the borehole 26 is being drilled. The communication sub 72 obtains the signals and measurements and transfers the signals, using two-way telemetry, for example, to be processed on the surface. Alternatively, the signals can be processed using a downhole processor in the drilling assembly 90.

The surface control unit or processor 40 also receives signals from other downhole sensors and devices and signals from sensors $S_1$–$S_3$ and other sensors used in the system 10 and processes such signals according to programmed instructions provided to the surface control unit 40. The surface control unit 40 displays desired drilling parameters and other information on a display/monitor 42 utilized by an operator to control the drilling operations. The surface control unit 40 preferably includes a computer or a microprocessor-based processing system, memory for storing programs or models and data, a recorder for recording data, and other peripherals. The control unit 40 is preferably adapted to activate alarms 44 when certain unsafe or undesirable operating conditions occur.

Figure 2:
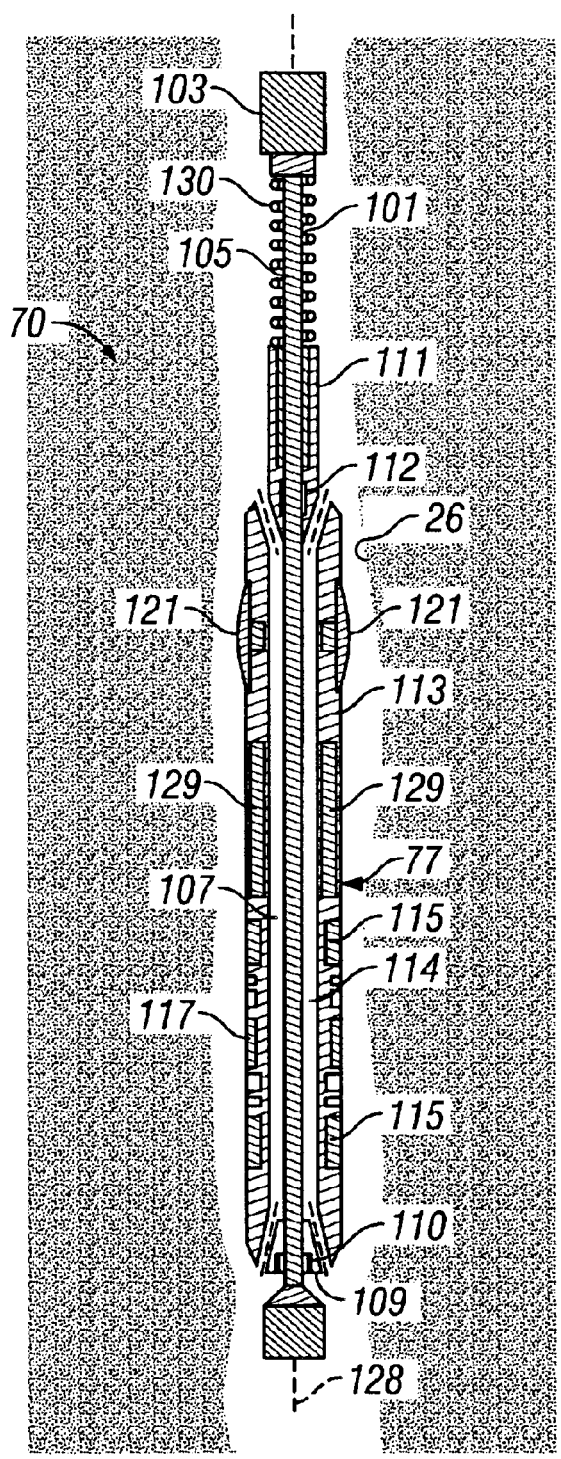
FIG. 2 (Prior Art) is a side-elevational view partially in cross-section of a drilling assembly including a sensor assembly in accordance with the present invention.

A suitable NMR device for use in the present invention is disclosed in U.S. Pat. No. 6,247,542 to Kruspe et al, the contents of which are fully incorporated herein by reference. This is shown in FIG. 2. A segment 70 of drill pipe 22, illustrated in greater illustrates the apparatus and method according to Kruspe including a sleeve member, such as a sensor assembly, slidably coupled to a longitudinal member, such as a section of drill pipe, wherein, when the sleeve member is non-rotating, the longitudinal member is free to rotate. The sleeve member may be held in a non-rotating position through engagement with the borehole wall and a decoupling of the sleeve member and the rotating drillstring. However, the apparatus and method according to the present invention can be adapted for any MWD device or tool typically used on a rotating drillstring.

Figure 3:
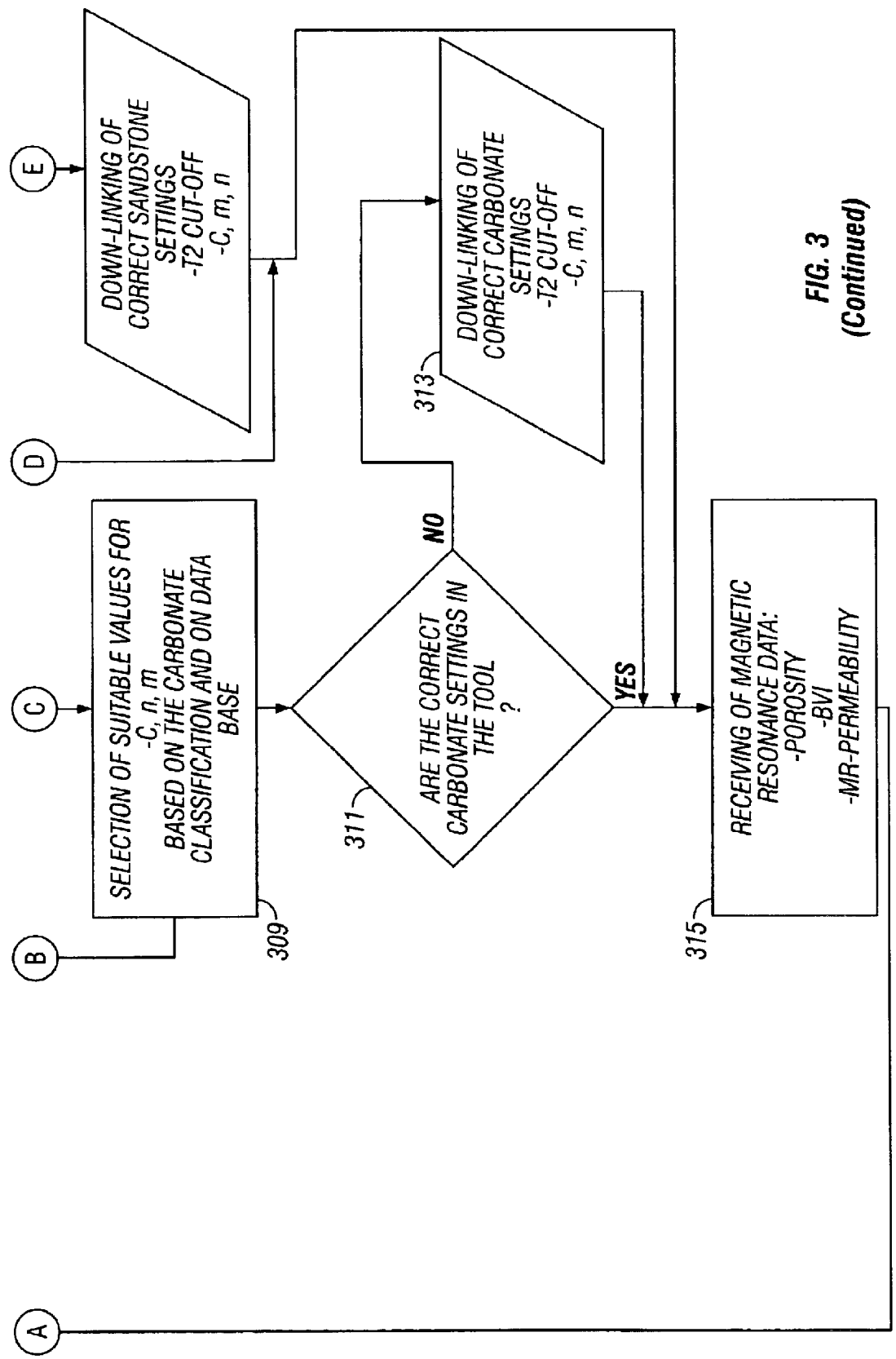
FIG. 3 shows a flowchart of the present invention.

The MWD tool 79, including an associated pulsed NMR tool 77 having a sensor assembly 113, and the pulsed power unit 78 are connected in tandem in the drilling assembly 90. The MWD tool 79 may also include a sonic sensor, a density measurement tool, and a porosity measurement tool. As seen in FIG. 3, the NMR tool 77 is rotationally symmetric about a longitudinal axis 128 of the drilling assembly 100. The longitudinal member is, for example, a drill pipe section 101, which forms the core of the segment 70. Alternatively, the longitudinal member is a shaft in a downhole directional drilling assembly. The drill pipe section 101 is connected to the drillstring 20 by the upper tool joint 103 and the lower tool joint 139, and has a channel or flow pass 105 for the drilling mud to flow downhole. The sensor assembly 113 surrounds the drill pipe section 101 and is slidably coupled to the longitudinal member or the drill pipe section 101. The sensor assembly 113 is coupled to the drill pipe section 101 by at least one of guide sleeves 109 and 111. The guide sleeves 109 and 111 include, for instance, slip rings and bearings 110 and 112, respectively. Alternatively, a single guide sleeve (not shown) including slip rings and bearings, is used, for example, centrally located between ends of the sensor assembly 113. The guide sleeves 109 and 111 allow the sensor assembly 113 to move freely in the axial direction and to a lesser extent laterally with respect to the drill pipe section 101. The sensor assembly 113 has an outer diameter that is somewhat less than the inner diameter of the borehole 26. For illustrative purposes, FIG. 2 shows the space between the sensor assembly 113 and the borehole wall in an exaggerated manner. The NMR sensor assembly includes flow paths 107 and 114 for return flow of the drilling mud from the drilling assembly 90 below wherein the gap between the sensor assembly 113 and the borehole wall are minimized.

The magnet assembly 115, for providing the static magnetic field, and the RF coil assembly 117 are disposed in the sensor assembly 113. The RF coil assembly 117 includes, for instance, at least one transmitter for transmitting a pulsed RF field into the formation. In the configuration as illustrated in FIG. 2, the RF field is axial and is orthogonal to the static field of the permanent magnet assembly 115 in a region of interest or examination outside the borehole for NMR signal measurements. However, the apparatus of the present invention is not limited to the illustrated sensor assembly 113. Any number of appropriate magnet arrangements and antenna or coil arrangements which provide a static magnetic field and an RF field orthogonal to the static magnetic field direction for creating the region of interest for NMR signal sensitivity can be used according to the present invention. For example, the NMR tool 77 can employ separate transmitter and receiver RF coils, located, for example, on the sensor assembly 113.

Typically, the RF coil assembly 117 is pulsed and creates a high frequency electromagnetic RF field orthogonal to the static magnetic field generated by the magnet assembly 115 and in the region of substantially uniform field strength creating the region or volume of interest for NMR signal sensitivity. The sensor assembly 113 detects the NMR signals resulting therefrom. Rock pores in the earth formations surrounding the wellbore are filled with fluid, typically water or hydrocarbon. The hydrogen nuclei in the fluid are aligned by the region of homogeneous magnetic field, generated by the magnet assembly 115. The hydrogen nuclei are then flipped away from the homogeneous magnetic field by the pulsed RF field produced by RF coil assembly 117. At the termination of the pulsed RF field from RF coil assembly 117, the hydrogen nuclei revolve or precess at high frequency around the homogeneous magnetic field inducing an NMR signal in the RF coil assembly 117 until the hydrogen nuclei relax to the original direction along the homogeneous magnetic field. The induced NMR signals are processed downhole or sent to the surface for processing.

Those versed in the art would recognize that, depending upon the configuration of the permanent magnet assembly 115, the region of examination could have one of a number of configurations. In one embodiment, the region of examination could be substantially toroidal shaped with the axis of the toroid along the longitudinal axis of the tool. In other configurations, the region of examination could be localized on opposite sides of the borehole or even on just one side of the borehole. It will also be clearly apparent to those skilled in the art that the static magnetic field area can also be obtained if the magnet assembly 115 includes dc-energized electromagnets, or superconducting dc electromagnets. All of these are intended to be within the scope of the present invention.

The NMR electronics 129 is housed in the NMR sensor assembly 113. The purpose of the NMR electronics 129 is to control the sensor assembly 113, record, process and transmit the recorded data, to the telemetry module 72. This can be done by means of electrical or acoustic telemetry by known devices and will not be discussed. A spring 130 having a cable conduit through the spring 130 allows power and data transmission via the guide sleeve 111 and slip ring through the cable conduit to and from the MWD tool 79. The MWD tool 79 also transmits data to the sensor assembly 113, for example, through mud pulse telemetry, and provides power from the power unit 78. The NMR electronics may also be referred to hereafter as a downhole processor, though it is to be understood that a downhole processor may be located at other positions in the downhole assembly.

The sensor assembly 113 is also provided with at least one clamping pad, clamping piston or ribs 121. The ribs 121 are capable of outward movement for locking the sensor assembly 113 to the borehole wall during measurement by the sensor assembly 113. In one embodiment, the ribs 121 are hydraulically activated. In the inactivated position of the ribs 121, the sensor assembly 113 rests on the lower tool joint 139 and is held up against gravitational pull by the spring 130 that is fixedly attached to the drill pipe section 101. Continued rotation of the drillstring 20 loosely carries the sensor assembly 113 along. In the activated position, the ribs 121 engage the borehole walls and prevent any further movement of the sensor assembly 113. Further rotation of the drillstring 20 does not affect the position of the sensor assembly 113 that remains in a clamped position against the borehole wall. In the clamped position, the sensor assembly 113 is essentially decoupled from rotational and vertical movement of the drillstring 20, enabling measurements, such as NMR measurements from the NMR sensor assembly 113, to be carried out without interference from tool motion and vibration. Due to the proximity of the borehole wall to the magnet assembly 115, the region of examination is within the formation and any signal from the borehole fluid is small. In typical operation, the NMR measurement takes between 0.01 to 1 second, during which time the drill pipe section 101 advances some distance. Once the NMR measurement has been completed, the ribs 121 are retracted, as a result of which the sensor assembly 113 is no longer coupled to the borehole wall. The sensor assembly 113 then drops down until any further downward motion is stopped by the spring 130. In another embodiment, the ribs 121 are actuated electrically, e.g., by a stepper motor. Other methods, such as those using springs, would be known to those versed in the art.

The device of Kruspe thus comprises a sensor assembly mounted on a slidable sleeve slidably coupled to a longitudinal member, such as a section of drill pipe. When the sensor assembly is held in a non-rotating position, for instance for obtaining the measurements, the longitudinal member is free to rotate and continue drilling the borehole, wherein downhole measurements can be obtained with substantially no sensor movement or vibration. This is particularly useful in making NMR measurements due to their susceptibility to errors due caused by tool vibration. A clamping device is used, for instance, to hold the sensor assembly in the non-rotating position.

The specific NMR sensor discloses in Kruspe et al has permanent magnets as well as RF antennas on the sleeve. A suitable sensor configuration is disclosed in U.S. Pat. No. 6,215,304 to Slade, the contents of which are fully incorporated herein by reference. The tool is rotationally symmetric, i.e., it measures 360° around the tool simultaneously. However, as noted in the Kruspe patent, other magnet and antenna configurations could be used. An advantage of using the Slade device is that usually no borehole correction is necessary because the tool is tuned to read only formation signal unless the hole is severely enlarged or the tool is off center1.

Data are acquired and processed using one of two schemes. The standard data acquisition and processing scheme uses methods that have been used in wireline logging. The acquisition and processing parameters for this are stored in the memory of the downhole processor and are described below. For analysis of carbonate reservoirs, drill cutting are analyzed at the surface by a geologist, and using one of the classification schemes described below, the geologist interprets the type of carbonate formation that is being drilled. This classification is sent by telemetry to the downhole processing module which then selects, from among the processing parameters stored in a suitable downhole memory, an acquisition and/or processing scheme suitable for the type of carbonate being drilled. Alternatively, the acquisition and processing parameters may be sent by telemetry to the downhole processor. Such a downlink telemetry system is taught in European Patent 744,527 of Oppelt et al. and U.S. Pat. No. 5,963,138 of Gruenhagen et al., having the same assignee as the present application.

FIG. 3 is a flowchart illustrating a preferred embodiment of the invention. At 301 the formation is drilled into by a measurement-while-drilling device conveying a magnetic resonance device in a borehole penetrating said formation. At 303, individual cuttings from the depth of the drilling device are investigated. These cuttings are brought to the surface by mud flow through the annulus between the drilling tubular and the borehole wall. Classification of individual cuttings can then be made by an operator, such as an on-site geologist. At 305, a decision is made to determine if the rock formation is carbonate or not.

If the formation is carbonate, then classification of the type of carbonate is made using an acceptable classification system, such as Dunham, Lucia, or Melim, for example. This classification is the procedure is depicted at 307. Due to the fact that the NMR logging is done using a sensor assembly that is a few feet from the drillbit, there is sufficient time for analysis of the cuttings at the surface and using suitable downlink telemetry to communicate the classification system to the downhole processor before the NMR sensor reaches the depth from which the drill cuttings were recovered. A suitable method can be used for determining the rate of penetration, such as that described in copending, commonly owned U.S. patent application Ser. No. 10/167,332, of Dubinksy et al, filed on Jun. 11, 2002, may be used. The contents of the Dubinsky application are incorporated herein by reference.

Figure 4A:
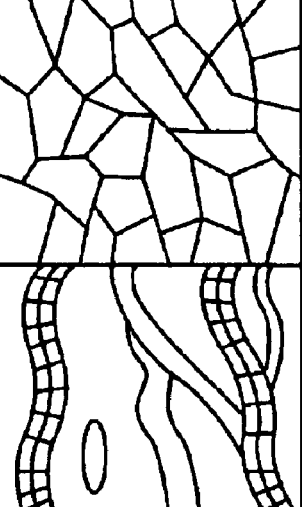
FIG. 4a (Prior Art) shows a typical classification scheme of carbonate rocks.

To digress briefly, FIG. 4a shows a typical methodology for determining that classification of carbonate rocks (Dunham classification). If depositional texture is not recognizable, the carbonate falls into a crystalline carbonate category. Otherwise if rocks are originally bound together during deposition, the carbonate falls under Boundstone. Otherwise, carbonates are categorized based on grain or mud support. Grain-supported rocks are classified as either Packstone or Grainstone, with Grainstone generally lacking mud, and Packstone containing mud, clay, and fine silt-size carbonate. Mud-supported carbonate rocks are classified as either MudStone or Wackestone, with Wackestone comprising more than 10% grains, and Mudstone comprising less that 10% grains.

Figure 4B:
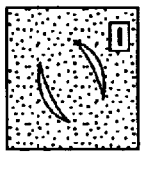
FIG. 4b (Prior Art) shows a classification scheme for carbonate rocks modified for use in petrophysical exploration.

FIG. 4b shows a modification of the Dunham classification for use in petrophysical classification. In the absence of vuggy porosity, pore-size distribution in carbonate rocks can be described in terms of particle size, sorting and interparticle porosity. The approach to size and sorting used in this petrophysical classification is similar to the grain-/mud-support principle upon which the Dunham's (1962) classification is built. Dunham's classification, however, is focused on depositional texture, whereas petrophysical classifications are focused on contemporary rock fabrics which include depositional and diagenetic textures. Therefore, minor modifications must be made in Dunham's classification before it can be applied to a petrophysical classification. Instead of dividing fabrics into grain support and mud support as in Dunham's classification, fabrics are divided into grain-dominated and mud-dominated. The important attributes of grain-dominated fabrics are the presence of open or occluded intergrain porosity and a grain-supported texture. The important attribute of mud-dominated fabrics is that the areas between the grains are filled with mud even if the grains appear to form a supporting framework.

Grainstone is clearly a grain-dominated fabric, but Dunham's Packstone class bridges a boundary between large intergrain pores in Grainstone and small interparticle pores in Wackestones and mudstones. Some Packstones have intergrain pore space and some have the intergrain spaces filled with mud. The Packstone textural class must be divided into two rock-fabric classes: grain-dominated Packstones that have intergrain pore space or cement and mud-dominated Packstones that have intergrain spaces filled with mud.

Dolomitization can change the rock fabric significantly. In limestones, fabrics can usually be distinguished with little difficulty. If the rock has been dolomitized, however, the overprint of dolomite crystals often obscures the precursor limestone fabric. Precursor fabrics in fine-crystalline dolostones are easily recognizable. However, as the crystal size increases, the precursor fabrics become progressively more difficult to determine. Grainstones and grain-dominated packstones are usually composed of grains much larger then the dolomite crystal size so that dolomitized grainstones are readily identified.

Dolomite crystals (defined as particles in this classification) commonly range in size from several microns to >200 microns. Micrite particles are usually <20 microns in size. Therefore, dolomitization of a mud-dominated carbonate fabric can result in an increase in particle size from <20 microns to >200 microns, and a corresponding increase in permeability as dolomite crystal size increases.

Returning to FIG. 3, at 309, NMR acquisition and processing parameters can be suitably selected based on the carbonate classification and on database values. Suitable parameters for selection of suitable values are identified here as (C, n, m) and are discussed further below. Previously determined values for C, n, and m of classified carbonates are stored and retrieved from a database, as represented at 321 and can be compiled previously for use in the invention. The database of 321 comprises data for carbonates from a large number of samples. From these samples, a lot of data concerning petrophysical properties, including Klinkenberg permeability measurements, thin section, core pictures, NMR measurements, capillary pressure curves, etc., are available. The method of Chen 1998 (see Chen, S; Ostroff, G. & Georgi, D. T (1998): *Improving Estimation of NMR Log $T_2$ cutoff value with core NMR and capillary pressure measurements.*—Society of Core Analysts Annual Conference and Exhibition, The Hague, Netherlands, SCA Paper 9822, p. 12.) can preferably be used to obtain values of $T_2$ cut-off. These are discussed further below.

Figure 5:
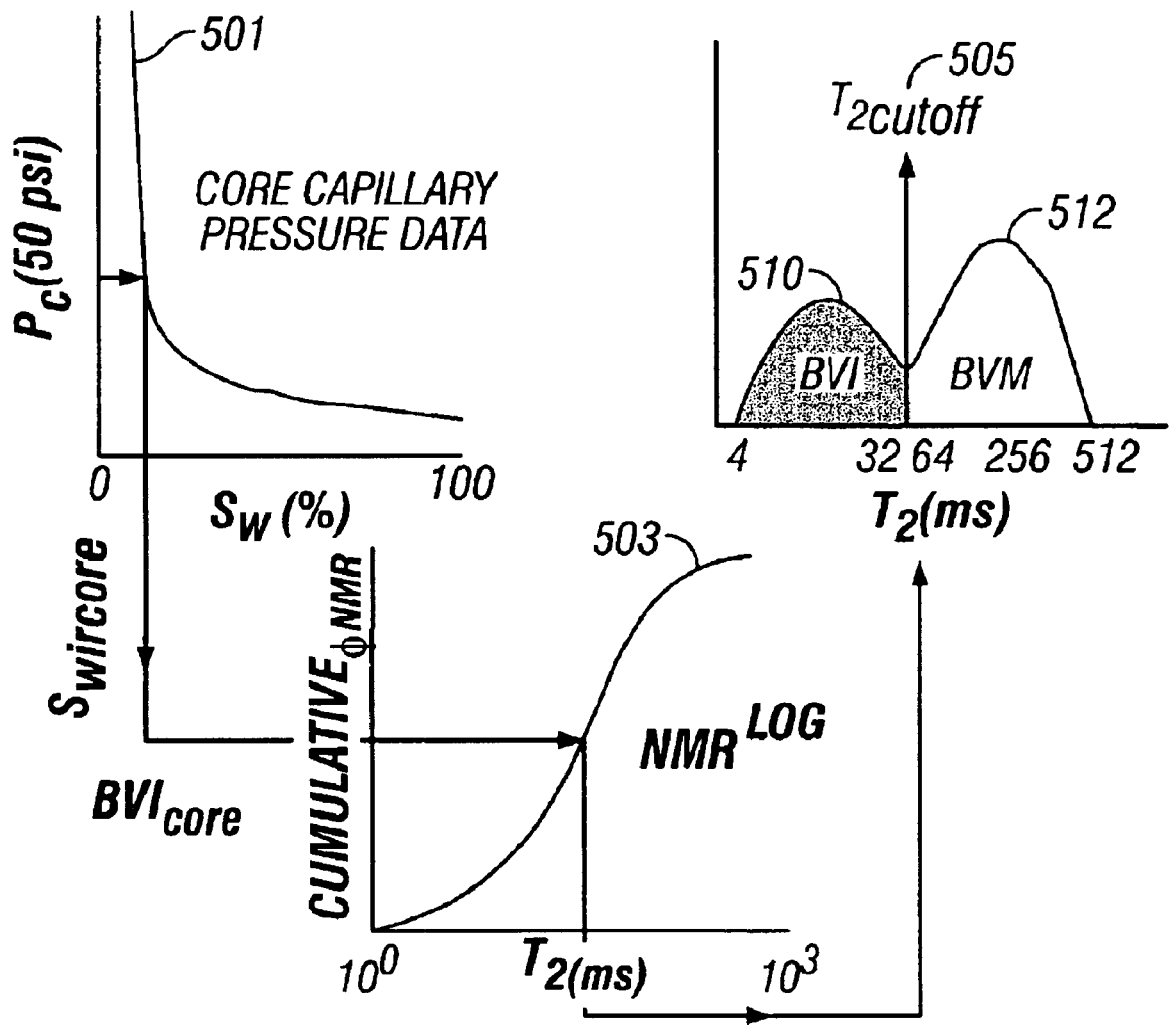
FIG. 5 (Prior Art) shows a method of determining the remaining irreducible water saturation in a rock.

As an example, FIG. 5 (prior art) shows how the bulk volume irreducible (BVI), remaining irreducible water saturation, can be determined with the corresponding capillary pressure curve using the method of Chen 1998. Capillary pressure curves 501 enable determining the remaining irreducible water saturation ($SW_{IRR}$) in the rock. Based on this, the bulk volume irreducible (BVI) 510 and the bulk volume moveable (BVM) 512 can be calculated. To calculate BVI based on these results the following formula is used:

$$BVI = \phi SW_{IRR}/100.$$

The calculated BVI value can be used to take the $T_2$ cut-off of the sample directly from the cumulated graph of the $T_2$ spectrum. The $T_{2\ cut\text{-}off}$ 505 is the cut-off between BVI 510 and BVM 512. To use the method of Chen, a conversion factor may be used to transform mercury pressure into water pressure $$P_{H_2O} = P_{Hg}/5.1$$

Typically, a $T_2$ value of 33 ms is used as a standard $T_2$ cut-off for sandstones. Classifying the carbonates and using the values derived with the method of Chen et all gives values such as those contained in Tables 1–3 for various classification systems. Tables such as these are included in the database 321 of FIG. 3. The tables below show $T_2$-cutoff values and theirs statistical significance using three types of classification.

TABLE 1

$T_2$ cutoffs based on Dunham classification

|  | Mean (ms) | Standard dev (ms) | Correlation coefficient r | r² |
|---|---|---|---|---|
| Mudstone-wackestone (23 samples) | 58.2 | 36.5 | −0.52 | 0.27 |
| Dolomitic mudstone-wackestone (5 samples) | 107.4 | 71.9 | 0.71 | 0.50 |
| Packstone (18 samples) | 51.3 | 41.1 | −0.43 | 0.19 |
| Dolomitic packstone (4 samples) | 35.8 | 16.7 | 0.37 | 0.14 |
| Grainstone (9 samples) | 185.6 | 261.6 | 0.82 | 0.68 |
| Dolomitic grainstone (3 samples) | 22.7 | 12.5 | −0.75 | 0.57 |
| Dolomite (32 samples) | 111.1 | 184.1 | 0.36 | 0.13 |

TABLE 2

$T_2$ cutoff values based on Lucia classification

|  | Mean (ms) | Std. Dev (ms) | Correlation Coefficient r | r² |
|---|---|---|---|---|
| Class 1 (21 samples) | 166.2 | 240.8 | 0.78 | 0.61 |
| Class 2 (27 samples) | 77.0 | 95.1 | 0.70 | 0.50 |
| Class 3 (46 samples) | 50.6 | 32.6 | −0.53 | 0.29 |

TABLE 3

$T_2$ cutoff values based on Melim classification

|  | Mean (ms) | Std. Dev. (ms) | Correlation coefficient r | r² |
|---|---|---|---|---|
| Primary Porosity |  |  |  |  |
| Intraparticle porosity (17 samples) | 44.7 | 39.2 | −0.36 | 0.13 |
| Interparticle porosity (12 samples) | 60.4 | 34.5 | −0.47 | 0.22 |
| Secondary Porosity |  |  |  |  |
| Intercrystalline porosity (30 samples) | 62.9 | 59.4 | 0.77 | 0.59 |
| Moldic pores (8 samples) | 72.4 | 33.4 | 0.92 | 0.85 |
| Vuggy pores (5 samples) | 442.9 | 444.3 | 0.98 | 0.95 |
| Filled pores (6 samples) | 24.1 | 12.0 | −0.98 | 0.96 |
| No visible pores (16 samples) | 118.9 | 109.91 | 0.54 | 0.29 |

Thus, in the present invention, the classification or the parameters based on the classification are sent downhole. Additionally, parameters derived from downhole measurements can be used to classify the carbonates directly in the downhole instrument. In this case, the classification process can be performed at least to a certain extent downhole. Since other sensors have different distances to the drill bit, the data of the formation in question is available earlier and can be derived from the downhole memory. In a preferred embodiment of the invention, classification based on more than one classification system may be used. The downhole processor then selects, or example, a T2 cutoff that gives the results for determination of BVI.

Building the database comprises:

(i) deriving permeability, porosity and core capillary pressure from laboratory measurements;
(ii) choosing a classification such that the statistically significance for the individual rock is highest and
(iii) determining parameters based on the classification which will be used for a later processing of the data derived in a downhole measurement.

Next, a best-fit solution for the two commonly used permeability calculations (Coates and Schlumberger-Doll-Research (SDR)) in the field of NMR measurement is performed, basing the calculations on the different classifications of carbonates. To calculate the permeability with the Coates equation, the total porosity of the NMR measurement and the relationship of BVI and BVM are used:

$$k_{Coates} = (\phi_{NMR}/C_1)^4 (BVM/BVI)^2$$

Permeability (k), $\phi_{NMR}$, BVM and BVI are already known terms from different measurements which could include laboratory measurements. The only unknown term in this equation is "$C_1$" (in some literature examples also described as "a"). Based on the used carbonate classification, one can look for a best-fit value for $C_1$ for the different carbonates in the database to improve the permeability determination.

The SDR equation uses total porosity and the logarithmic mean value of T2 from the NMR measurement to calculate the permeability:

$$k_{SDR} = C_2 (\phi_{NMR}/100)^4 (T_2 \log(\text{mean})).$$

Permeability (k), $\phi_{NMR}$, $T_2$log(mean) are already known terms from different measurements. The only unknown term in this equation is "$C_2$" (in some literature examples also described as "b"). Based on the used carbonate classification, one can select a best-fit value for $C_2$ for the different carbonates to improve the permeability determination. Further optimization of the permeability equations can be done by modifying the exponents (commonly referred to as n and m).

Correlation coefficient between the Klinkenberg permeability (as a dependent value) and the calculated permeability for optimized Coates and SDR are determined. for samples in the database. The table below shows how for some classified carbonates (e.g. grainstone), SDR is better and has a higher correlation ($r^2=0.9$ for SDR, compared to $r^2=0.12$ with Coates). For a practical application, a decision tree can be developed to determine when and which classification to use, and to apply the appropriate permeability calculation to get the most accurate permeability results.

Returning now to FIG. 3, In Box 311, a decision is made as to the correctness of the carbonate settings in the tool. If the settings are not correct, then correct carbonate settings (i.e. $T_2$ cut-off, $-C$, m, n) can be down-linked, as occurs in Box 313. If the settings in Box 311 are correct, Box 315 is performed immediately. In Box 315, Magnetic Resonance data is received and determination can be made for formation properties, such as porosity, BVI, MR, and permeability. These processed values can then be sent uphole by telemetry.

Figure 6A:
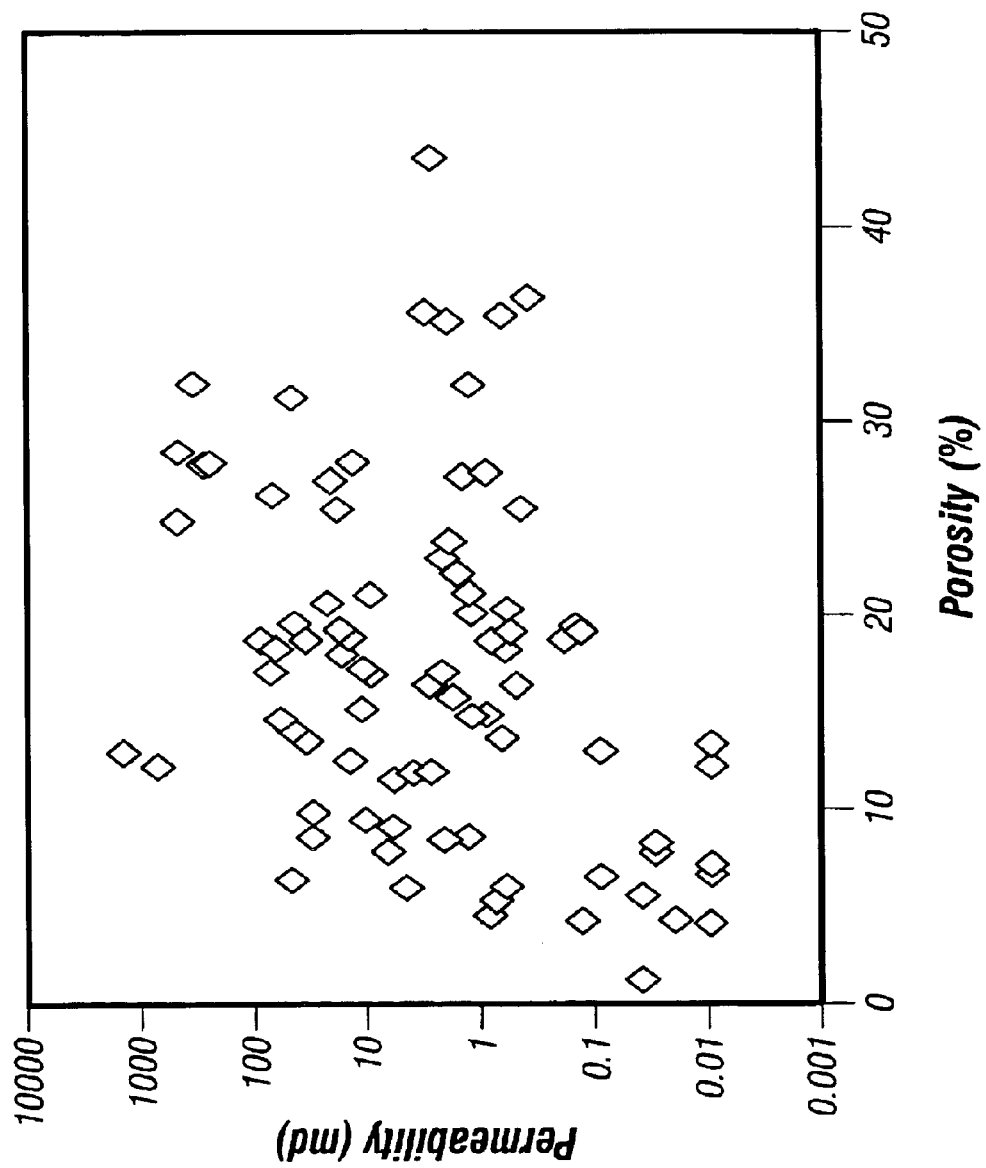
FIGS. 6a–6d show plots of permeability vs. porosity of carbonate rock formation without classification, and with using classification systems of Dunham, Lucia, and Melim, respectively.
Figure 6B:
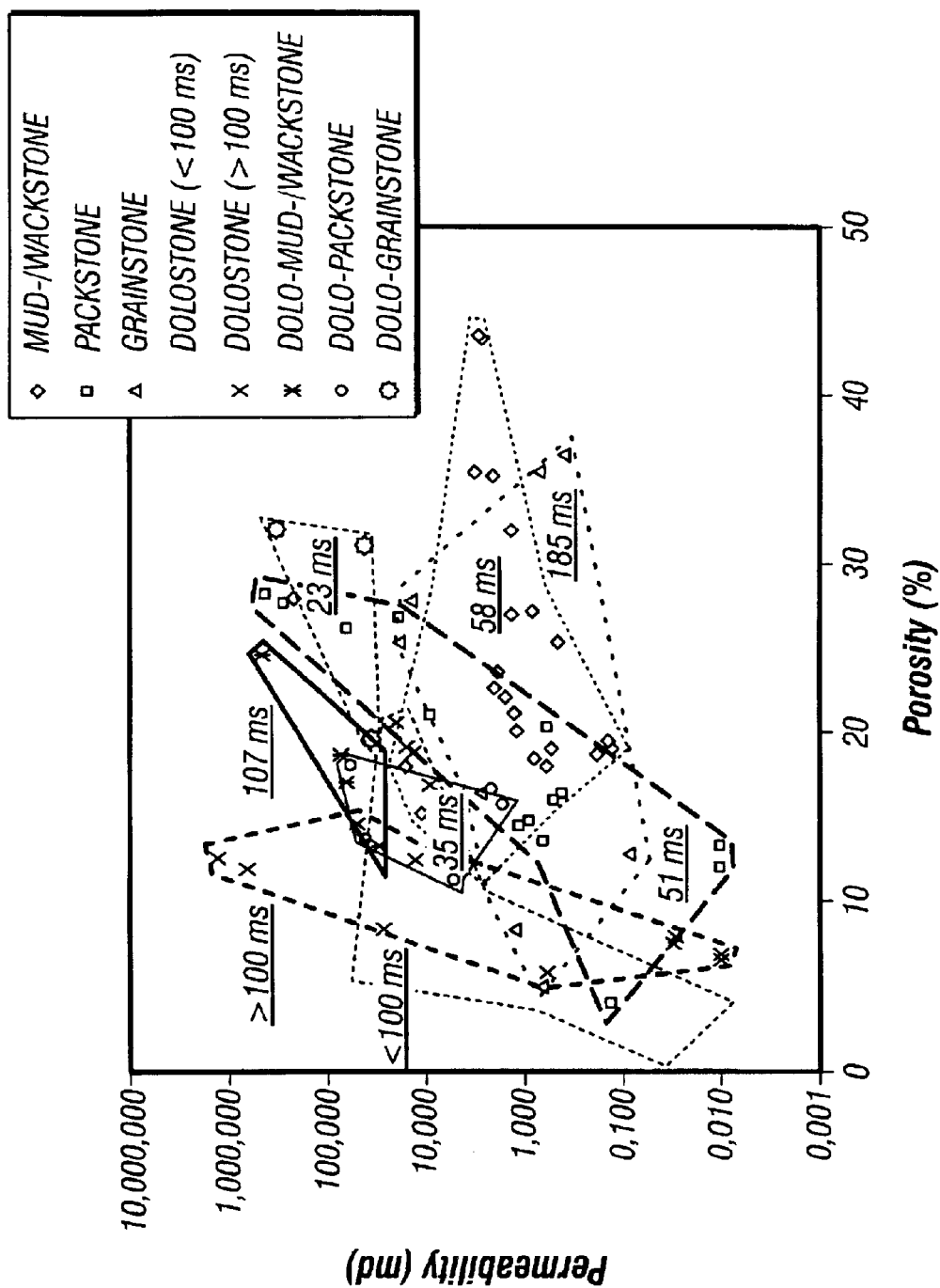
Figure 6C:
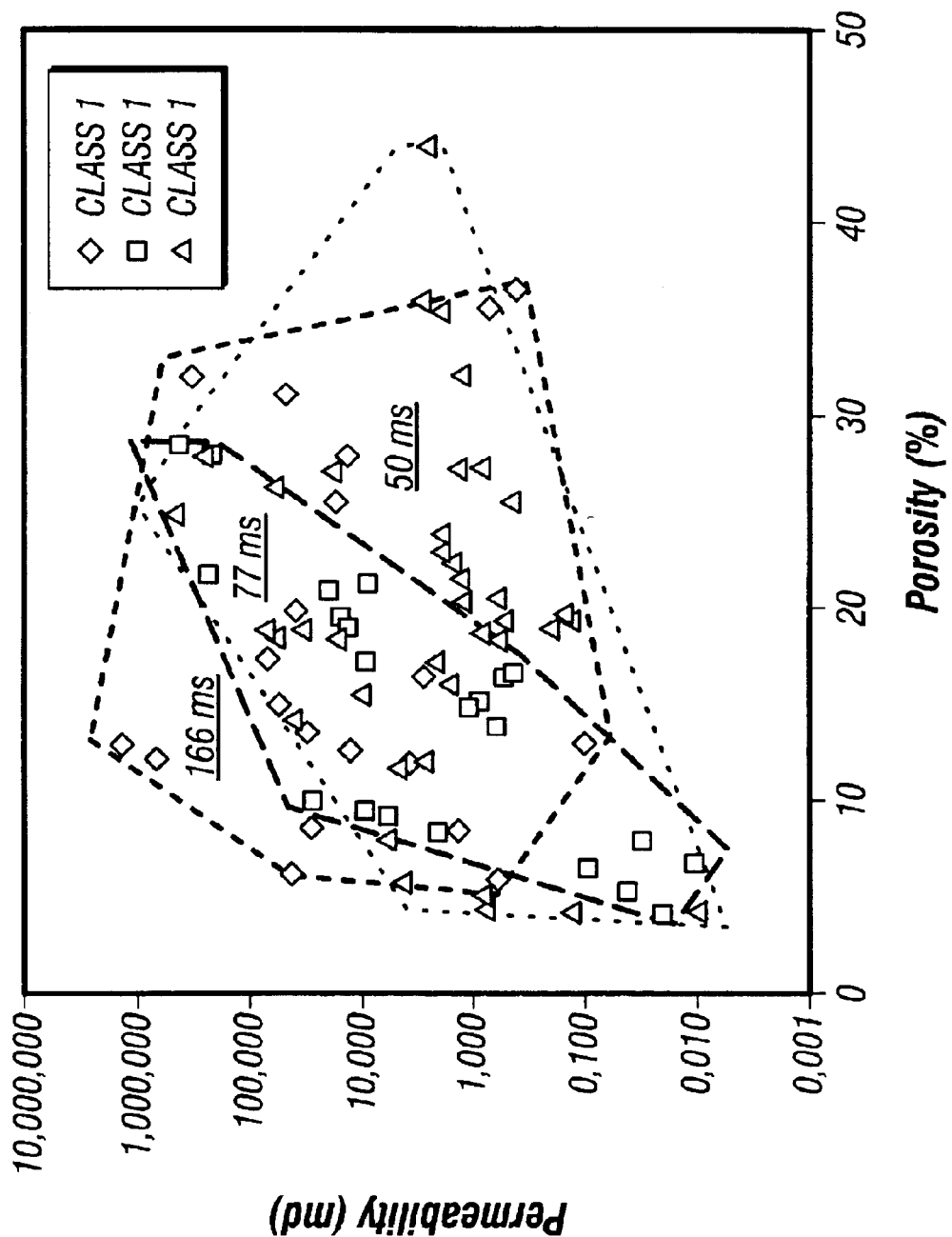
Figure 6D:
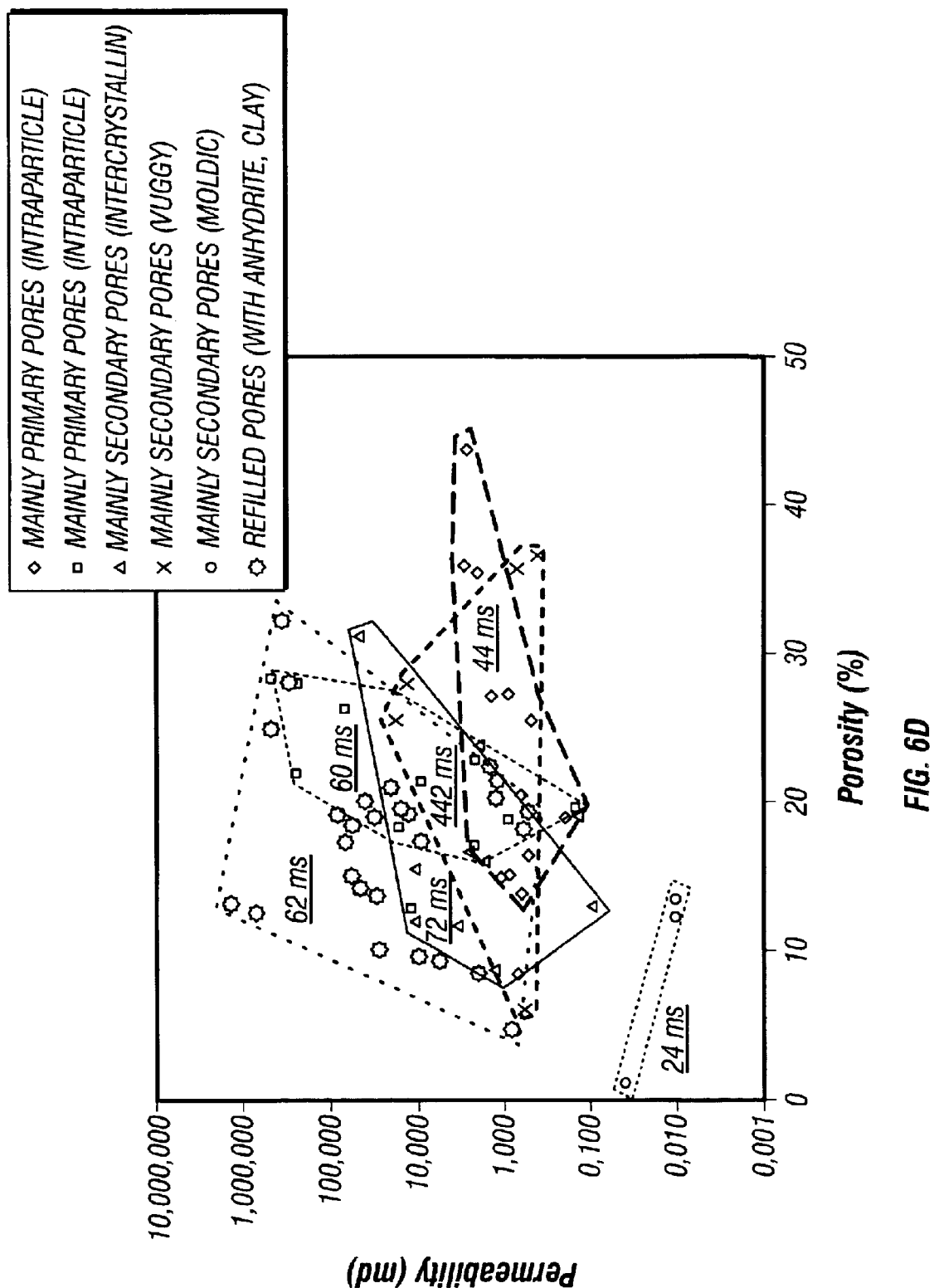

FIG. 6a shows a plot of Permeability vs. Porosity as is typical in prior art. NMR measurements can enable the operator with the ability to create a plot such as shown in FIG. 6a. However, such plotting without use of a classification scheme results in either poor correlation or no correlation between the two parameters. Results from Box 315 enable the operator to perform the same plot and under a classification scheme, i.e. Dunham, Lucia, etc., thereby enabling a correlation of permeability to porosity through use of said classification scheme. Examples of said correlation using classification schemes are shown in FIGS. 6b, 6c, and 6d. FIG. 6b shows the data of FIG. 6a upon using the method of the invention with the application of the Dunham classification scheme. FIG. 6c employs the Lucia classification scheme, and FIG. 6d employs the Melim classification scheme. Applying Lucia's classification, for example, leads to different classes in different porosity permeability ranges. This information can be combined with NMR measurements to obtain more accurate $T_2$ cut-off for carbonates, better indication which permeability equation (SDR, Coates, etc.) will provide better results for the classified carbonates, and to optimize the measurement sequences.

Figure 7:
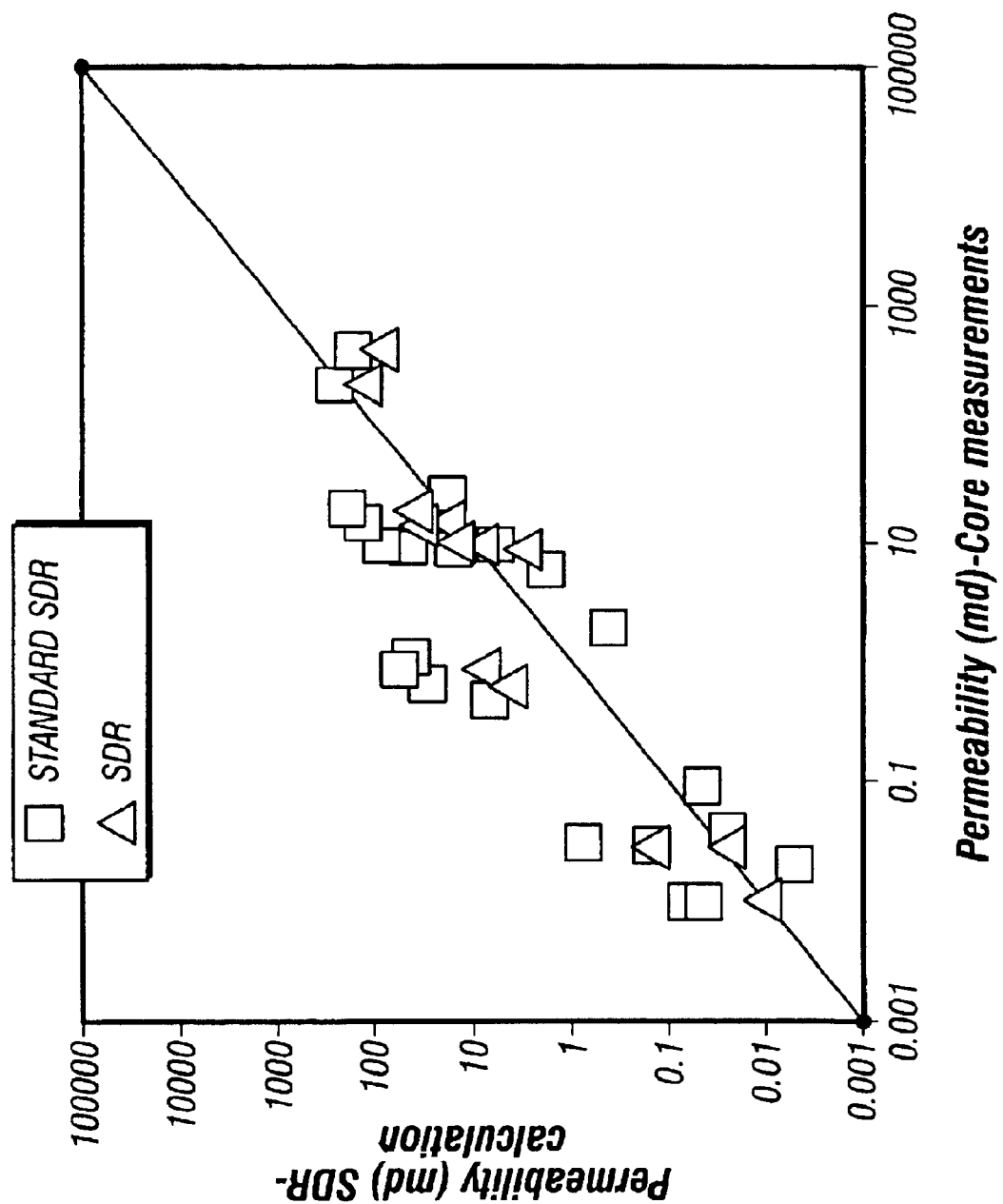
FIG. 7 show a measured permeability using Klinkenberg with the NMR permeability before and after application of a classification scheme.

FIG. 7 shows measured permeability using Klinkenberg with the NMR permeability before and after the application of a Lucia classification scheme. In FIG. 7, the classification scheme is Lucia and is for packstone. The higher correlation is seen upon applying optimized SDR equation.

Figure 8:
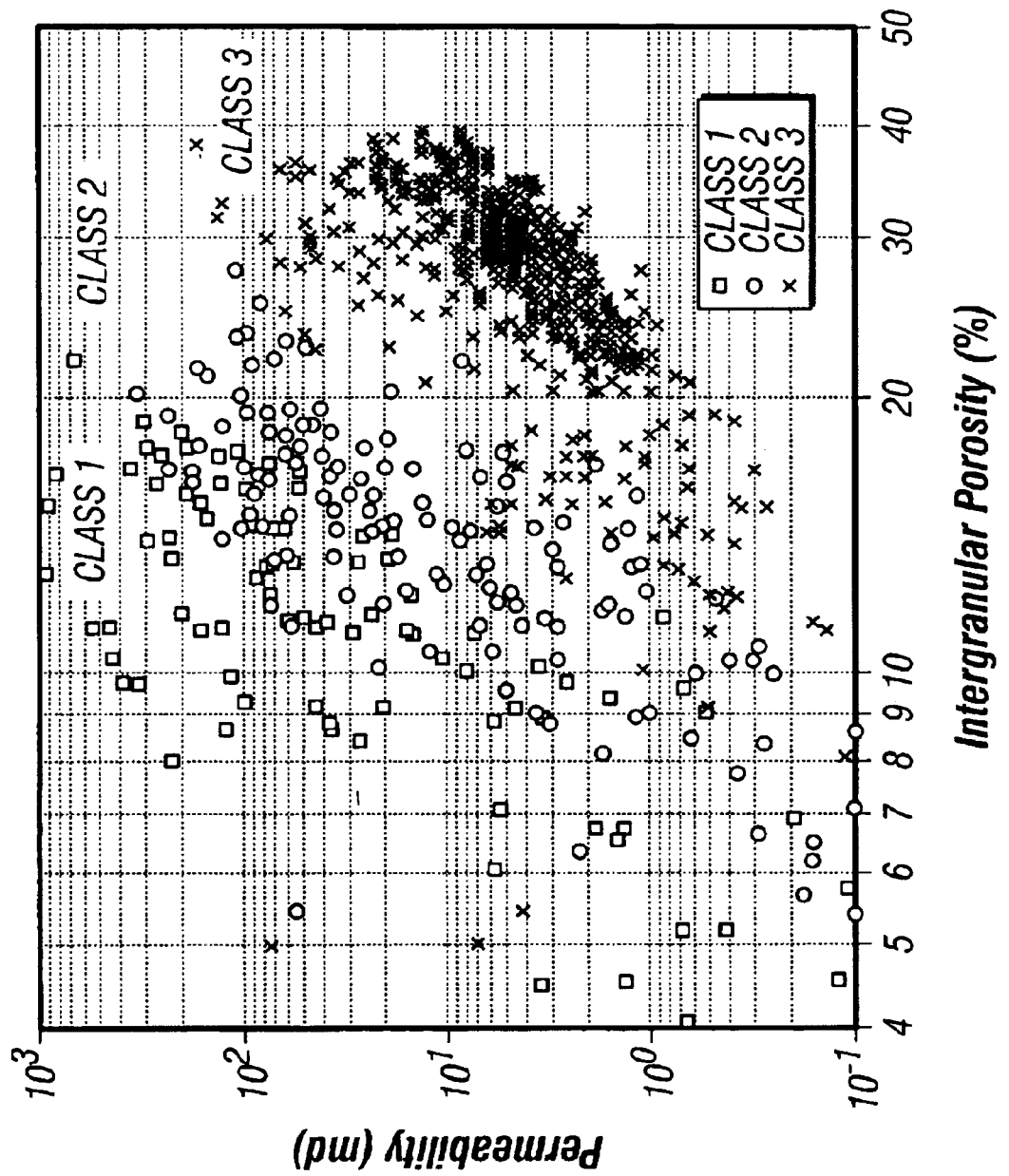
FIG. 8 shows a plot of permeability vs. porosity of carbonate rock formation including the use of a Lucia classification scheme.

FIG. 8, taken from Lucia 1999 (see Lucia, F. J. (1999): *Carbonate Reservoir Characterization*. Springer, Berlin, Heidelberg, New York. p. 226) shows the areas of high correlation that appear upon applying a classification scheme. The Lucia classification scheme is used in FIG. 8. A difference is seen in different porosity and permeability ranges. Based on results of FIG. 8, it is possible to combine this information with NMR measurements to achieve: more accurate $T_{2\ cut-off}$ for carbonates, better indication of which permeability equation will provide better results for the classified carbonates, and an optimized measurement sequence.

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A method of determining a parameter of interest of an earth formation including a carbonate, the method comprising:

(a) using a nuclear magnetic resonance (NMR) sensor assembly conveyed in a borehole in said earth formation for obtaining nuclear magnetic resonance (NMR) spin-echo signals from a region of examination in said earth formation, said spin-echo signals indicative of the parameter of interest;

(b) using a classification scheme for obtaining a class of said carbonate;

(c) processing said spin-echo signals using said obtained class for obtaining the parameter of interest.

2. The method of claim 1 wherein said sensor assembly is part of a logging tool on a bottom hole assembly used for drilling said borehole.

3. The method of claim 2 wherein using said classification scheme further comprises examination of cuttings brought to a surface location by a drilling mud conveyed in said borehole.

4. The method of claim 3 wherein said downhole measurements are selected from such measurements as Natural Gamma Ray, Resistivity, Density, Nuclear porosity, acoustic porosity and formation pressure tester.

5. The method of claim 1 wherein said sensor assembly is part of a logging tool conveyed on a wireline into said borehole.

6. The method of claim 1 wherein obtaining said spin-echo signals further comprises:

(i) using a magnet on said sensor assembly for producing a static magnetic field in a region of interest in said earth formation;

(ii) using an antenna on said sensor assembly for producing a pulsed radio-frequency (RF) magnetic field in said region of interest and inducing said spin echo signals; and (iii) using an antenna on said sensor assembly for detecting said spin-echo signals.

7. The method of claim 1 wherein using said classification scheme further comprises downhole analysis of of downhole measurements derived from other sensors.

8. The method of claim 1 wherein processing said spin-echo signals further comprises using a downhole processor.

9. The method of claim 8 wherein using said downhole processor further comprises using processing parameters obtained from at least one of (i) parameters sent by telemetry to the downhole processor, and, (ii) parameters retrieved from a downhole storage device based at least in part on using class information.

10. The method of claim 8 wherein said processing parameter includes at least one of (i) a cutoff time $T_{2cutoff}$ of a transverse relaxation time of said spin echo signals, (ii) a cutoff time $T_{1cutoff}$ of a longitudinal relaxation time of said spin echo signals, said cutoff times differentiating between a bound volume irreducible (BVI) and a bound water moveable (BVM).

11. The method of claim 10 wherein said cutoff times are based at least in part on measurements on a core sample.

12. The method of claim 1 wherein said parameter of interest includes at least one of (i) a total porosity, (ii) a bound volume irreducible (BVI), (iii) a bound water moveable (BVM), (iv) a distribution of transverse relaxation times and, (v) a distribution of longitudinal relaxation times.

13. The method of claim 12 wherein said parameter of interest further includes a permeability of said carbonate, the method further comprising using a relationship between said permeability and at least one of:

(A) a cutoff time $T_{2cutoff}$ of a transverse relaxation time of said spin echo signals, (B) a cutoff time $T_{1cutoff}$ of a longitudinal relaxation time of said spin echo signals, said cutoff times differentiating between a bound volume irreducible (BVI) and a bound water moveable (BVM).

14. The method of claim 13 wherein said relationship is defined by one of (i) the Coates equation, (ii) the SDR equation (iii) Kozeny-Carman based equation, and, (iv) a Sum of Echos based equation.

15. The method of claim 14 further comprising selecting one of said equations using said obtained class.

16. The method of claim 12 further comprising sending a value of a determined parameter to a surface location by telemetry.

17. The method of claim 1 further comprising using said obtained class for determining an acquisition parameter used for obtaining said NMR spin-echo signals.

18. The method of claim 17 wherein said obtained class is telemetered from a surface location.

19. The method of claim 17 wherein said obtained class is determined from downhole measurements.

20. A system for determining a parameter of interest of an earth formation including a carbonate, the system comprising:

(a) a measurement device conveyed in a borehole in said earth formation for obtaining nuclear magnetic resonance (NMR) spin-echo signals from a region of examination in said earth formation, said spin-echo signals indicative of the parameter of interest; and (b) a downhole processor for processing said spin-echo signals using an obtained class of said carbonate for obtaining the parameter of interest.

21. The system of claim 20 wherein said sensor assembly is part of a logging tool on a bottom hole assembly (BHA) used for drilling said borehole.

22. The system of claim 21 wherein said sensor assembly further comprises:

(i) a magnet for producing a static magnetic field in a region of interest in said earth formation;

(ii) a first antenna for producing a pulsed radio-frequency (RF) magnetic field in said region of interest and inducing said spin echo signals; and (iii) a second antenna for detecting said spin-echo signals.

23. The system of claim 22 wherein at least one of said magnet, said first antenna, and said second antenna are on a non-rotating sleeve of said BHA.

24. The system of claim 22 wherein said first and second antennas are the same.

25. The system of claim 20 wherein said processor is further adapted for using a processing parameter obtained from at least one of (i) parameters sent by telemetry to the downhole processor, and, (ii) parameters retrieved from a downhole storage device based at least in part on using class information.

26. The system of claim 20 wherein said processing parameter includes at least one of (i) a cutoff time $T_{2cutoff}$ of a transverse relaxation time of said spin echo signals, (ii) a cutoff time $T_{1cutoff}$ of a longitudinal relaxation time of said spin echo signals, said cutoff times differentiating between a bound volume irreducible (BVI) and a bound water moveable (BVM).

27. The system of claim 26 wherein said cutoff times are based at least in part on measurements on a core sample.

28. The system of claim 20 wherein said parameter of interest includes at least one of (i) a total porosity, (ii) a bound volume irreducible (BVI), (iii) a bound water moveable (BVM), (iv) a distribution of transverse relaxation times and, (v) a distribution of longitudinal relaxation times 29. The system of claim 28 wherein said parameter of interest further includes a permeability of said carbonate, and wherein the processor is further adapted for using a relationship between said permeability and at least one of at least one of (A) a cutoff time $T_{2cutoff}$ of a transverse relaxation time of said spin echo signals, (B) a cutoff time $T_{1cutoff}$ of a longitudinal relaxation time of said spin echo signals, said cutoff times differentiating between a bound volume irreducible (BVI) and a bound water moveable (BVM).

30. The system of claim 20 wherein said downhole processor further determines an acquisition parameter used for acquisition of said NMR spin-echo signals based on said obtained class.

31. The system of claim 30 wherein said downhole processor further obtains said obtained class from downhole measurements.

* * * * *